United States Patent [19]

Saito et al.

[11] Patent Number: 5,210,315

[45] Date of Patent: May 11, 1993

[54] PROCESS FOR PRODUCING α-HYDROXYKETONES

[75] Inventors: Takao Saito; Hidenori Kumobayashi, both of Tokyo; Shunichi Murahashi, Osaka, all of Japan

[73] Assignee: Takasago International Corporation, Tokyo, Japan

[21] Appl. No.: 779,529

[22] Filed: Oct. 18, 1991

[30] Foreign Application Priority Data

Oct. 20, 1990 [JP] Japan .................................. 2-280586
Jan. 31, 1991 [JP] Japan .................................. 3-29341

[51] Int. Cl.$^5$ ............................................. C07C 45/27
[52] U.S. Cl. .................................... 568/385; 558/311; 558/442; 560/53; 560/174; 560/231; 560/266; 560/254; 560/256; 552/542
[58] Field of Search ....................... 568/311, 342, 385; 552/542; 560/53, 174, 231, 266, 234, 256

[56] References Cited

U.S. PATENT DOCUMENTS

| | | | |
|---|---|---|---|
| 3,337,635 | 8/1967 | Norton et al. ....................... | 568/385 |
| 3,518,285 | 6/1970 | Fenton et al. ....................... | 568/385 |
| 3,879,467 | 4/1975 | Zajocek et al. ....................... | 568/385 |
| 4,609,763 | 9/1986 | Griggs et al. ....................... | 568/385 |

*Primary Examiner*—James H. Reamer
*Attorney, Agent, or Firm*—Sughrue, Mion, Zinn, Macpeak & Seas

[57] ABSTRACT

A process for producing an α-hydroxyketone represented by formula (I):

$$R^1-\overset{O}{\underset{}{C}}=\underset{\underset{R^2}{|}}{\overset{OH}{\overset{|}{C}}}-R^3 \qquad (I)$$

wherein $R^1$ represents a substituted or unsubstituted alkyl group, a substituted or unsubstituted aralkyl group, or an alkoxycarbonyl group; and $R^2$ and $R^3$ each represent a hydrogen atom, a substituted or unsubstituted alkyl group, or a substituted or unsubstituted aralkyl group, provided that they do not simultaneously represent a hydrogen atom; or a pair of $R^1$ and $R^2$, a pair of $R^1$ and $R^3$, or a pair of $R^2$ and $R^3$ is taken together to form a ring; and the pair of $R^1$ and $R^2$ and the pair of $R^2$ and $R^3$ may form a ring simultaneously, is disclosed, comprising reacting a compound represented by formula (II):

$$R^1-\overset{H}{\underset{}{C}}=\underset{\underset{R^2}{|}}{\overset{}{C}}-R^3 \qquad (II)$$

wherein $R^1$, $R^2$, and $R^3$ are as defined above, with an oxidizing agent in the presence of a ruthenium compound and water. α-Hydroxyketones useful as physiologically active substances are produced with good selectivity and in high yield.

2 Claims, No Drawings

PROCESS FOR PRODUCING α-HYDROXYKETONES

FIELD OF THE INVENTION

This invention relates to a process for producing α-hydroxyketones which widely occur in nature and are of great importance for their physiological activities. For example, Adriamycin and Daumycin are known as anticancer agents (see *J. Am. Chem. Soc.*, Vol. 85, p. 5334 (1964)); Betamethasone and Cortisone are known as steroid hormones (see *J. Am. Chem. Soc.*, Vol. 80, p. 6687 (1958)); and Cyproterone is known as an antiandrogenic (see Ger Offen, No. 1189, p. 91 (1965)).

BACKGROUND OF THE INVENTION

Known processes for synthesizing these α-hydroxyketones include, for example, oxidation of diols (see *J. Organomet. Chem.*, Vol. 5, p. 263 (1966)), oxidative cleavage of epoxides (see *J. Org. Chem.*, Vol. 26, p. 1681 (1961)), and acyloin condensation (see *J. Org. Chem.*, Vol. 40, p. 393 (1975)) and, in addition, synthesis from olefins using a stoichiometric amount of potassium permanganate.

On the other hand, ruthenium compounds are known to catalyze oxidation reaction of a certain kind of organic compounds as reported in *Kacaku*, Vol. 45, No. 6, pp. 426–427, Kagaku Dojin K.K. (1990). In view of the specificity of their catalytic activity, it has been quite unexpected that ruthenium compounds also exert a catalytic action on olefin oxidation for production of α-hydroxyketones.

SUMMARY OF THE INVENTION

An object of the present invention is to provide a process for producing α-hydroxyketones by oxidation of olefins with good selectivity and in high yield.

As a result of extensive studies, the inventors have found that the above object of the present invention is accomplished by using a ruthenium compound as a catalyst.

The present invention relates to a process for producing an α-hydroxyketone represented by formula (I):

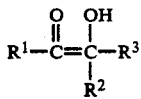
(I)

wherein $R^1$ represents a substituted or unsubstituted alkyl group, a substituted or unsubstituted aralkyl group, or an alkoxycarbonyl group; and $R^2$ and $R^3$ each represent a hydrogen atom, a substituted or unsubstituted alkyl group, or a substituted or unsubstituted aralkyl group, provided that they do not simultaneously represent a hydrogen atom; or a pair of $R^1$ and $R^2$, a pair of $R^1$ and $R^3$, or a pair of $R^2$ and $R^3$ is taken together to form a ring; and the pair of $R^1$ and $R^2$ and the pair of $R^2$ and $R^3$ may form a ring simultaneously, which comprises reacting a compound represented by formula (II):

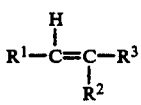
(II)

wherein $R^1$, $R^2$, and $R^3$ are as defined above, with an oxidizing agent in the presence of a ruthenium compound and water.

DETAILED DESCRIPTION OF THE INVENTION

In formulae (I) and (II), the substituted alkyl group includes acetoxyalkyl, 3-methyl-5-acetoxypentyl, benzyloxymethyl, and benzoyloxyethyl groups. The substituted aralkyl group includes an acetoxybenzyl group. The alkoxycarbonyl group includes methoxycarbonyl and ethoxycarbonyl groups.

Specific examples of the olefin represented by formula (II) which can be used as a starting material in the present invention are cyclopentene, cyclohexene, cyclooctene, trans-2-butene, cis-2-butene, 4-octene, β-methylstyrene, cyclohexadiene, cyclooctadiene, indene, 1-methylcyclopentene, 1-methylcyclohexene, ethylidenecyclohexane, 2-methyl-4,4-dimethylpentene, methyl crotonate, ethyl crotonate, methyl cinnamate, ethyl 3-methylcrotonate, pentylidenecyclohexane, and ethylidenecyclopentane.

The ruthenium compound which can be used as a catalyst in the present invention includes those listed below which are described in *Comprehensive Organometallic Chemistry*, Vol. 4, pp. 651–930, Pergamon Press (1982):

1) Ruthenium compounds represented by formula (III):

wherein X represents a halogen atom, an acyloxy group of the formula, $R^4COO$ (wherein $R^4$ represents a lower alkyl group), or an acetylacetonato group.

Specific examples of such ruthenium compounds are ruthenium trichloride, ruthenium tribromide, and ruthenium triiodide, and hydrates thereof, trisacetylacetonatoruthenium, and ruthenium acetate.

2) Ruthenium complexes:
(i) Ruthenium-phosphine complexes, e.g.,
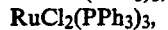
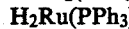
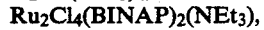
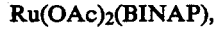
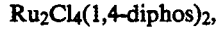
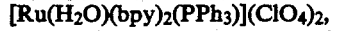
wherein Et represents an ethyl group; Ph represents a phenyl group; Ac represents an acetyl group; BINAP represents a 2,2'-bis(diphenylphosphino)-1,1'-binaphthyl group; 1,4-diphos represents 1,4-bis(diphenylphosphino)butane; and bpy represents a bipyridyl group; hereinafter the same.
(ii) Ruthenium-nitrosyl complexes, e.g.,
(iii) Ruthenium-carbonyl complexes, e.g.,
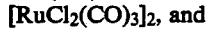
(iv) Ruthenium-oxo complexes, e.g.,
Ruthenium-olefin complexes, e.g.,
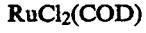

wherein COD represents 1,5-cyclooctadiene, hereinafter the same.

3) Metallic ruthenium powders including: - ruthenium-on-carbon, ruthenium-on-graphite, ruthenium-on-alumina, ruthenium-on-silica, ruthenium-on-zeolite, and ruthenium-on-zirconia.

The ruthenium compound as a catalyst is usually used in an amount of from 0.01 to 0.2 mole, and preferably from 0.03 to 0.1 mole, per mole of the starting olefin.

The oxidizing agent which can be used in the present invention is not particularly limited. Suitable oxidizing agents include various peracids, e.g., peracetic acid, perpropionic acid, and m-chloroperbenzoic acid. Any commercially available oxidizing agent may be used, or an oxidizing agent to be used may be prepared from a carboxylic acid and hydrogen peroxide before the reaction.

The oxidizing agent is usually used in an amount of from 1 to 8 mole, and preferably from 2 to 3 mole, per mole of the starting olefin.

In carrying out the process of the present invention, a compound (II), water, and a ruthenium compound are dissolved or suspended in an appropriate solvent, such as acetonitrile, methylene chloride, dichloroethane, chlorobenzene, and mixtures thereof, and to the solution or suspension is added a solution of a peracid in ethyl acetate or acetic acid at a temperature of from -10° to +30° C. while stirring. While the order or manner of addition of the starting compound, the catalyst, etc. is not particularly restricted, it is preferable to add the oxidizing agent finally.

Isolation of a reaction product from the reaction mixture can be effected by known separation means such as distillation and column chromatography.

The present invention is now illustrated in greater detail with reference to Examples, but it should be understood that the present invention is not deemed to be limited thereto. All the percents are by weight unless otherwise indicated.

EXAMPLE 1

In a 50 ml flask equipped with a thermometer, a dropping funnel, and a stirrer were charged 10 ml of methylene chloride, 10 ml of acetonitrile, 10 ml of water, 0.82 g (10 mmole) of cyclohexene, and 78 mg (0.3 mmole) of $RuCl_3 \cdot 3H_2O$. The mixture was cooled to 18° C. with stirring on a magnetic stirrer, and a 30% ethyl acetate solution of 7.6 g (30 mmole) of peracetic acid was added thereto dropwise over 2 hours. After stirring at room temperature for 2 hours, the reaction mixture was extracted three times with 50 ml portions of methylene chloride. The combined extract was washed with 50 ml of a saturated sodium chloride aqueous solution and dried over anhydrous magnesium sulfate. The solvent was removed by distillation to obtain 0.843 g (percent yield: 74%) of 2-hydroxycyclohexanone (α-hydroxycyclohexanone).

$^1$H-NMR (CDCl$_3$, 270 MHz) δppm: 1.45 -1.93 (m, 4H), 2.10 (m, 1H), 2.32 (m, 3H), 3.65 (b, 1H), 4.12 (ddd, J=11.9, 6.8, 1.5, 1H)

$^{13}$C-NMR (CDCl$_3$, 67.5 MHz) δppm: 23.4, 27.6, 36.8, 39.5, 75.4, 211.3

EXAMPLE 2

In a 50 ml flask equipped with a thermometer, a dropping funnel, and a stirrer were charged 10 ml of methylene chloride, 10 ml of acetonitrile, 10 ml of water, 1.12 g (10 mmole) of 4-octene, and 78 mg (0.3 mmole) of ruthenium trichloride, and a 30% ethyl acetate solution of 7.6 g (30 mmole) of peracetic acid was added to the mixture dropwise at 15° C. over 1.5 hours while stirring on a magnetic stirrer. After the addition, the stirring was further continued at room temperature for 2 hours. The reaction mixture was extracted three times with 30 ml portions of methylene chloride. The combined extract was washed with 30 ml of a saturated sodium chloride aqueous solution and dried over anhydrous magnesium sulfate. The solvent was removed by distillation to obtain crude 5-hydroxy-4-octanone, which was then purified by silica gel column chromatography using a 10:1 (by volume) mixture of n-hexane and ethyl acetate as an eluent to give 0.87 g (percent yield: 59%) of 5-hydroxy-4-octanone.

$^1$H-NMR (CDCl$_3$, 270 MHz) δppm: 0.94 (t, J=7.5, 3H), 0.97 (t, J=7.3, 3H), 1.40 (b, 1H), 1.48 (m, 2H), 1.66 (tq, J=5 1, 7.3, 2H), 1.72 (m, 2H), 2.45 (dt, J=7.2 (gem.), 5.1, 2H), 4.18 (t, J=3.5, 1H)

$^{13}$C-NMR (CDCl$_3$, 67.5 MHz) δppm: 13.6, 13.8, 17.2, 18.2, 35.9, 39.8, 76.3, 212.5

EXAMPLE 3

In a 50 ml flask equipped with a thermometer and a dropping funnel were charged 10 ml of methylene chloride, 10 ml of acetonitrile, 5 ml of water, 0.82 g (10 mmole) of cyclohexene, and 277 mg (0.3 mmole) of HRuCl(PPh$_3$)$_3$ in a nitrogen atmosphere. To the mixture was added dropwise a 30% ethyl acetate solution of 7.6 g (30 mmole) of peracetic acid at 20° C. over 2 hours while stirring. After the addition, the stirring was further continued at room temperature for 1 hour, and the mixture was worked up in the same manner as in Example 1 to obtain 0.68 g (percent yield: 60%) of 2-hydroxycyclohexanone (α-hydroxycyclohexanone).

$^1$H-NMR The same as in Example 1.

EXAMPLES 4 TO 12

Compounds shown in Table 1 below were synthesized in the same manner as in Example 1. The NMR spectra of the compounds are also shown.

TABLE 1

| Example No. | Substrate | Reaction Product | Percent Yield (%) | $^1$H-NMR Spectrum (CDCl$_3$, 270 MHz) δ (ppm) | $^{13}$C-NMR Spectrum (CDCl$_3$, 67.5 MHz) δ (ppm) |
|---|---|---|---|---|---|
| 4 | cyclooctene | 2-hydroxycyclo-octanone* | 42 | 0.95(m, 1H), 1.30–2.10 (m, 7H), 2.36(m, 3H), 2.75 (ddd, J=3.9, 12.0 12.0, 1H), 3.80(b, 1H, OH), 4.18 (dd, J=2.9, 6.6, 1H) | 22.1, 24.6, 25.6, 28.9, 29.1, 37.3, 76.2, 217.4 |
| 5 | β-methyl-styrene | 1-phenyl-1-oxo-2-propanol | 62 | 1.45(d, J=7.1, 3H), 3.77 (d, J=5.4, 1H), 5.15(dq, J=5.4, 7.1, 1H), 7.30–7.95 (m, 5H) | 22.3, 69.4, 127.4, 128.4, 128.8, 129.0, 134.0. 138.1, 202.4 |
|  |  | 1-phenyl-2-oxo-1-propanol |  | 2.08(s, 3H), 4.28(d, J= 3.9, 1H), 5.09(d, J=3.9, | 25.2, 80.2, 128.7, 128.9, 129.0, |

TABLE 1-continued

| Example No. | Substrate | Reaction Product | Percent Yield (%) | $^1$H-NMR Spectrum (CDCl$_3$, 270 MHz) δ (ppm) | $^{13}$C-NMR Spectrum (CDCl$_3$, 67.5 MHz) δ (ppm) |
|---|---|---|---|---|---|
| 6 | indene | 2-hydroxy-1-indanone | 54 | 1H), 7.30–7.95(m, 5H) 3.01(dd, J=16.6, 5.1, 1H), 3.27(b, 1H), 3.56(dd, J= 16.6, 5.1, 1H), 4.54(dd, J=7.8, 5.1, 1H), 7.39–7.77 (m, 4H) | 133.5, 207.1 35.2, 74.3, 124.5, 126.8, 128.0, 134.1, 135.9, 151.0, 206.5 |
| 7 | 1,3-cyclohexadiene | 6-hydroxy-2-cyclohexen-1-one | 41 | 1.88(m, 1H), 2.41(m, 1H), 2.54(m, 2H), 3.70(b, 1H), 4.20(dd, J=13.7, 5.6, 1H), 6.12(ddd, J=9.8, 3.7, 1.8, 1H), 7.02(m, 1H) | 25.7, 31.3, 72.9, 127.0, 152.0, 200.4 |
| 8 | 1-methylcyclopentene | 2-hydroxy-2-methylcyclopentan-1-one | 68 | 1.26(s, 3H), 1.82(m, 1H), 2.01(m, 2H), 2.33(m, 2H), 2.56(b, 1H) | 17.3, 23.0, 34.3, 36.9, 76.6, 219.9 |
| 9 | 1-methylcyclohexane | 2-hydroxy-2-methylcyclohexan-1-one | 67 | 1.46(s, 3H), 1.60–1.80(m, 4H), 2.12(m, 2H), 2.50(m, 2H), 3.93(b, 1H) | 23.0, 25.1, 27.9, 37.8, 42.1, 76.4, 214.3 |
| 10 | ethylidenecyclohexane | 1-acetylcyclohexan-1-ol | 55 | 1.40–1.80(m, 10H), 2.24 (s, 3H), 3.50(b, 1H) | 20.5, 23.7, 25.3, 33.9, 78.1, 212.7 |
| 11 | ethyl crotonate | ethyl 2-hydroxy-3-oxobutyrate | 56 | 1.32(t, J=7.0, 3H), 2.35 (s, 3H), 4.30(q, 2H, J= 7.0), 4.30(b, 1H), 4.77 (s, 1H) | 14.1, 26.0, 62.6, 78.3, 168.3, 202.0 |
| 12 | methyl cinnamate | methyl 2-hydroxy-3-oxo-3-phenyl-propionate | 23 | 3.72(s, 3H), 4.30(b, 1H), 5.61(s, 1H), 7.43–8.12(m, 5H) | 50.1, 74.4, 128.9, 129.5, 130.1, 134.7, 149.1, 193.7 |

Note:
*Produced as an amorphous powder having a melting point of 140–145° C.

EXAMPLES 13 TO 22

In a 50 ml flask equipped with a thermometer, a dropping funnel, and a stirrer were charged 7 ml of methylene chloride, 7 ml of water, 2 mmole of 1-methyl-1-cyclohexene, and 0.1 mmole of each of ruthenium catalysts shown in Table 2 below. To the mixture was added dropwise a 30% ethyl acetate solution of 1.52 g (6 mmole) of peracetic acid at room temperature over 2 hours while stirring on a magnetic stirrer. After the addition, the stirring was further continued at room temperature for 2 hours. The reaction mixture was extracted three times with 20 ml portions of methylene chloride. The extract was washed with 30 ml of a saturated sodium chloride aqueous solution and dried over anhydrous magnesium sulfate. The solvent was removed by distillation, and the residual crude product was purified by silica gel column chromatography using a 5:1 (by volume) mixture of n-hexane and ethyl acetate as an eluent to obtain 2-methyl-2-hydroxy-1-cyclohexanone. The percent yield of the product is shown in Table 2.

TABLE 2

| Example No. | Ruthenium Catalyst | Percent Yield (%) |
|---|---|---|
| 13 | RuCl$_3$.3H$_2$O | 67 |
| 14 | Ru(NO)Cl$_3$.H$_2$O | 59 |
| 15 | RuCl$_2$(PPh$_3$)$_3$ | 55 |
| 16 | Ru(OAc)$_3$ | 52 |
| 17 | Ru(acac)$_3$* | 47 |
| 18 | RuO$_2$ | 42 |
| 19 | RuCl$_2$(COD) | 39 |
| 20 | Ru$_3$(CO)$_{12}$ | 32 |
| 21 | RuH$_2$(PPh$_3$)$_4$ | 20 |
| 22 | 5% Ru-on-alumina** | 11 |

Note:
*"acac" means acetylacetonato.
**The catalyst weighed 20 mg.

EXAMPLES 23 TO 34

Compounds shown in Table 3 below were synthesized in the same manner as in Example 1.

TABLE 3

| Example No. | Substrate | Reaction Product | Percent Yield (%) |
|---|---|---|---|
| 23 | 6-acetoxy-1-cyclohexane | 3-acetoxy-2-hydroxycyclohexanone | 70 |
| 24 | cholesterol acetate | 5-hydroxy-5-oxocholesterol acetate | 28 |
|  |  | 5,6-epoxycholesterol acetate | 25 |
| 25 | 4-acetoxy-5-methyl-2-hexene | 4-acetoxy-2-hydroxy-5-methyl-3-hexanone | 14 |
|  |  | 4-acetoxy-3-hydroxy-5-methyl-2-hexanone | 28 |
| 26 | 6-acetoxy-4-nonene | 6-acetoxy-4-hydroxy-5-nonanone | 18.8 |
|  |  | 6-acetoxy-5-hydroxy-4-nonanone | 33.2 |
| 27 | 1-acetoxy-1-phenyl-2-butene | 1-acetoxy-3-hydroxy-1-phenyl-2-butanone | 15.1 |
|  |  | 4-acetoxy-3-hydroxy-4-phenyl-2-butanone | 37.9 |
| 28 | 1-acetoxy-3-methyl-2-butene | 1-acetoxy-3-hydroxy-3-methyl-2-butanone | 78 |
| 29 | 2-acetoxy-1-ethylidene-cyclohexane | 1-(2-acetoxy-1-oxoethyl)-1-cylcohexanol | 70 |
| 30 | 2-acetoxy-1-ethylidene-cyclopentane | 1-(2-acetoxy-1-hydroxy-ethyl)-1-cyclopentanol | 70 |
|  |  | 1-(2-acetoxy-1-oxoethyl)-1-cyclopentanol | 63 |
| 31 | 2-(2-acetoxy-1-ethylidene)-1,2,3,4-tetrahydronaphthalene | 2-(acetoxy-1-oxoethyl)-2-hydroxy-1,2,3,4-tetrahydronaphthalene | 43 |
| 32 | 1-citronellyl acetate | (6S)-8-acetoxy-2,3-epoxy-2,6-dimethyloctane | 7 |

TABLE 3-continued

| Example No. | Substrate | Reaction Product | Percent Yield (%) |
|---|---|---|---|
| | | (6R)-8-acetoxy-2-hydroxy-2,6-dimethyl-3-octanone | 27 |
| 33 | 1-benzoyloxy-3-methyl-2-butene | 1-benzoyloxy-3-hydroxy-3-methyl-2-butanone | 54 |
| 34 | 1-benzyloxy-3-methyl-2-butene | 1-benzyloxy-3-hydroxy-3-methyl-2-butanone | 51 |

The present invention thus provides an industrially advantageous process for producing α-hydroxyketones useful as physiologically active substances or intermediates therefor through simple procedures, with good reaction selectivity, and in high yield.

While the invention has been described in detail and with reference to specific examples thereof, it will be apparent to one skilled in the art that various changes and modifications can be made therein without departing from the spirit and scope thereof.

What is claimed is:

1. A process for producing an α-hydroxyketone represented by formula (I):

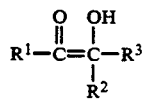

(I)

wherein R' represents a substituted or unsubstituted alkyl group, wherein the substituent for the substituted alkyl group is a benzyloxy group, an acyloxy group, or a benzoyloxy group, a substituted or unsubstituted aralkyl group, wherein the substituent for the aralkyl group is an acyloxy group, or an alkoxycarbonyl group; and $R^2$ and $R^3$ each represent a hydrogen atom, a substituted or unsubstituted alkyl group, wherein the substituent for the substituted alkyl group is a benzyloxy group, an acyloxy group, or a benzoyloxy group, or a substituted or unsubstituted aralkyl group, wherein the substituent for the aralkyl group is an acyloxy group, provided that they do not simultaneously represent a hydrogen atom; or a pair of $R^1$ and $R^2$, a pair of $R^1$ and $R^3$, or a pair of $R^2$ and $R^3$ is taken together to form a 5-to 8-membered ring; and the pair of $R^1$ and $R^2$ and the pair of $R^2$ and $R^3$ may form a 5- to 8-membered ring simultaneously, which comprises reacting a compound represented by formula (II):

(II)

wherein $R^1$, $R^2$, and $R^3$ are as defined above, with a peracid in the presence of a ruthenium compound, water, and a solvent, wherein said ruthenium compound is a compound represented by formula (III): wherein X represents a halogen atom, an acyloxy group of the formula, $R^4COO$, wherein $R^4$ represents a lower alkyl group, or an acetylacetonato group, wherein said solvent is selected from acetonitrile, methylene chloride, dichloroethane, chlorobenzene or mixtures thereof, the catalyst is used in an amount of 0.01 to 0.2 mole per mole of the compound represented by formula (II), the peracid is used in an amount of 1 to 8 moles per mole of the compound represented by formula (II), and the reaction temperature is −10° C. to +30° C.

2. A process as claimed in claim 1, wherein the substituted alkyl group represented by $R^1$, $R^2$ and $R^3$ is acetoxyalkyl, 3-methyl-5-acetoxypentyl, benzoyloxymethyl or benzoyloxyethyl, and the substituted aralkyl group represented by $R^1$, $R^2$ and $R^3$ is acetoxybenzyl, and the alkoxycarbonyl group is methoxycarbonyl or ethoxycarbonyl.

* * * * *

UNITED STATES PATENT AND TRADEMARK OFFICE
CERTIFICATE OF CORRECTION

PATENT NO. : 5,210,315

DATED : May 11, 1993

INVENTOR(S) : Takao SAITO, et al.

It is certified that error appears in the above-indentified patent and that said Letters Patent is hereby corrected as shown below:

On the title page, in the Abstract, Formula (I), column 1, lines 45-49, and column 7, lines 26-31 (claim 1), delete the existing structural formula (I) and insert therefor

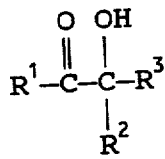

Signed and Sealed this

Fourth Day of October, 1994

Attest:

BRUCE LEHMAN

Attesting Officer

Commissioner of Patents and Trademarks